(12) United States Patent
Johnson et al.

(10) Patent No.: US 8,692,202 B2
(45) Date of Patent: Apr. 8, 2014

(54) GAS EXCHANGE SYSTEM FLOW CONFIGURATION WITH THERMALLY INSULATED SAMPLE CHAMBER

(75) Inventors: Mark A. Johnson, Hickman, NE (US); Andrew S. Parr, Lincoln, NE (US); Robert D. Eckles, Malcolm, NE (US)

(73) Assignee: Li-Cor, Inc., Lincoln, NE (US)

( * ) Notice: Subject to any disclaimer, the term of this patent is extended or adjusted under 35 U.S.C. 154(b) by 134 days.

(21) Appl. No.: 13/149,709

(22) Filed: May 31, 2011

(65) Prior Publication Data

US 2012/0074325 A1    Mar. 29, 2012

Related U.S. Application Data

(63) Continuation-in-part of application No. 12/889,289, filed on Sep. 23, 2010.

(51) Int. Cl.
*G01J 5/02*    (2006.01)

(52) U.S. Cl.
USPC .......................................................... 250/343

(58) Field of Classification Search
USPC .................... 250/343, 339.01–339.09, 339.1, 250/339.11–339.15
See application file for complete search history.

(56) References Cited

U.S. PATENT DOCUMENTS

| | | | |
|---|---|---|---|
| 4,312,218 A | | 1/1982 | Eckles |
| 4,768,390 A | | 9/1988 | Baker et al. |
| 4,803,370 A | | 2/1989 | Eckles |
| 5,077,469 A | * | 12/1991 | Fabinski et al. ............... 250/345 |
| 5,220,402 A | * | 6/1993 | Harvey ......................... 356/246 |
| 5,332,901 A | | 7/1994 | Eckles et al. |
| 5,340,987 A | | 8/1994 | Eckles et al. |
| 5,457,320 A | * | 10/1995 | Eckles et al. ................. 250/345 |
| 5,793,044 A | * | 8/1998 | Mace et al. ................... 250/343 |
| 5,932,877 A | * | 8/1999 | Braig et al. ................... 250/343 |
| 6,317,212 B1 | | 11/2001 | Eckles et al. |

(Continued)

FOREIGN PATENT DOCUMENTS

JP    55-047437 A    4/1980

OTHER PUBLICATIONS

Joanna C. Rooke, Christophe Meunier, Alexandre Léonard, and Bao-Lian Su, Title: Energy from photobioreactors: Bioencapsulation of photosynthetically active molecules, organelles, and whole cells within biologically inert matrices. Date: 2008, Publisher: Pure Appl. Chem., vol. 80, No. 11, pp. 2345-2376, 2008.*

(Continued)

*Primary Examiner* — David Porta
*Assistant Examiner* — Taeho Jo
(74) *Attorney, Agent, or Firm* — Gerald T. Gray; Leydig, Voit & Mayer LLP (57) ABSTRACT

System flow path designs that minimize the impact of gas diffusion sources and sinks. By reducing the magnitude of parasitic sources and sinks, lower rates of photosynthesis and transpiration can be more accurately measured, e.g., without the need for extensive empirical compensation. The gas exchange analysis system includes a sample chamber having an inlet and an outlet, wherein the internal surface(s) of the chamber defining the measurement volume are metal plated. The system also typically includes a source of gas coupled with the inlet of the sample chamber, and a gas analyzer coupled with the outlet of the sample chamber and configured to measure a concentration of one or more gases exiting the chamber, whereby the metal plated internal surface(s) of the chamber reduces sorption of the one or more gases within the chamber.

11 Claims, 8 Drawing Sheets

(56) References Cited

U.S. PATENT DOCUMENTS

| | | | |
|---|---|---|---|
| 7,063,667 B1* | 6/2006 | Ben-Oren et al. | 600/532 |
| 7,323,687 B2* | 1/2008 | Nanko et al. | 250/343 |
| 7,748,253 B2 | 7/2010 | Furtaw et al. | |
| 2003/0214372 A1 | 11/2003 | Miura et al. | |
| 2007/0246653 A1* | 10/2007 | Zhou | 250/339.1 |
| 2008/0277586 A1* | 11/2008 | Cardinale | 250/339.13 |
| 2008/0304979 A1 | 12/2008 | Lucas | |
| 2010/0028977 A1 | 2/2010 | Ng et al. | |
| 2010/0110437 A1 | 5/2010 | Furtaw et al. | |
| 2010/0262382 A1* | 10/2010 | Lighton | 702/24 |
| 2012/0073355 A1 | 3/2012 | Johnson et al. | |
| 2012/0074324 A1 | 3/2012 | Genty et al. | |

OTHER PUBLICATIONS 6400-22L Lighted Conifer Chamber | LI-COR Environmental NewsLine, Date: Jul. 2009, http://www.licor.com/env/newsline/2009/07/6400-22l.*

Robert W. Pearcy and Jeffrey R. Seemann, Title: Photosynthetic Induction State of Leaves in a Soybean Canopy in Relation to Light Regulation of Ribulose-1-5—Bisphophate Carboxylase and Stomatal Conductance, Date: Jun. 11, 1990, Publisher: Plant Physiol.*

Christopher B. Field, f. Timothy Ball and Joseph A. Berry, Title: Photosynthesis: principles and field techniques.*

Using the LI-6400/LI-6400XT Version 6', LI-COR Bioscience, Inc., Publication No. 9806-122, (Jul. 31, 1998).

Using the LI-6400/LI-6400XT Version 6', LI-COR Bioscience, Inc., Publication No. 9806-122, (Nov. 2008).

International Search Report and Written Opinion for PCT/US2011/052724 issued Apr. 23, 2012.

International Search Report and Written Opinion for PCT/US2011/052821 issued Apr. 24, 2012.

Non-Final Office Action issued May 21, 2012 in U.S. Appl. No. 12/889,289.

Non-Final Office Action issued Oct. 23, 2012 in U.S. Appl. No. 12/889,289.

* cited by examiner

Fig. 1a

FIG. 2 Sensor head with leaf chamber blocked off

FIG. 3 CO2 Diffusion with leaf chamber sealed off. Flow is split at console.

FIG. 4 Sensor head with flow split at the head

Figure 8. External view of plated part.

Figure 9. Sectioned plated part to show successful plating of internal passageways

GAS EXCHANGE SYSTEM FLOW CONFIGURATION WITH THERMALLY INSULATED SAMPLE CHAMBER

CROSS-REFERENCES TO RELATED APPLICATIONS

The present application is a continuation-in-part of U.S. patent application Ser. No. 12/889,289, filed Sep. 23, 2010, which is hereby incorporated by reference in its entirety for all purposes.

BACKGROUND

The present invention relates generally to gas exchange measurement systems, and more particularly to open photosynthesis measurement systems having an optimized flow configuration to minimize errors resulting from gas diffusion.

Systems for measuring plant photosynthesis and transpiration rates can be categorized as open or closed systems. For open systems, the leaf or plant is enclosed in a chamber, and an air stream is passed continuously through the chamber. $CO_2$ and $H_2O$ concentrations of chamber influent and effluent are measured, and the difference between influent and effluent concentration is calculated. This difference is used, along with the mass flow rate, to calculate photosynthesis ($CO_2$) and transpiration ($H_2O$) rates. For closed systems, the leaf or plant is enclosed in a chamber that is not supplied with fresh air. The concentrations of $CO_2$ and $H_2O$ are continuously monitored within the chamber. The rate of change of this concentration, along with the chamber volume, is used to calculate photosynthesis ($CO_2$) and transpiration ($H_2O$) rates.

In both open and closed systems, it is important that the leaf or plant be the only source or sink of both $CO_2$ and $H_2O$. $CO_2$ or $H_2O$ concentration changes not caused by the plant are a measurement error. These errors can be empirically compensated, for example as described in the LI-COR Biosciences LI-6400 User Manual (pp. 4-43 thru 4-48; included herein as Appendix A). Some instrument users may not understand the significance of these corrections, and neglect them.

The ability to regulate $CO_2$ and $H_2O$ concentrations in and around the sample is critical to accurate photosynthesis and transpiration measurements, and is a key function of the leaf chamber. The ideal chamber must not impact the dynamic control or measurement of $CO_2$ and $H_2O$ concentrations. A well known artifact of chamber construction is the uncontrolled release or retention of $CO_2$ or $H_2O$ by chamber surfaces. This phenomenon is generally known as sorption, and describes both adsorption and desorption. Adsorption is the retention of $H_2O$ or $CO_2$ molecules on the chamber surfaces. Desorption is the release of $H_2O$ or $CO_2$ molecules from the chamber surfaces. Both open and closed systems contain a circuit of pneumatic components (e.g., pumps, valves, chambers, tubing, analyzers, etc.). When $CO_2$ and $H_2O$ concentrations are dynamically changing, sorption on these components can provide an apparent $CO_2$ or $H_2O$ source and/or sink. Under steady-state conditions, sorption is not an active source or sink, and parasitic $CO_2$ and $H_2O$ sources and/or sinks can be attributed to bulk leaks and diffusion.

Bulk leaks are driven by pressure differentials between the system and the ambient environment. Proper system design and construction, along with inherently low operating pressures, generally minimize parasitic sources and sinks due to bulk leaks. Diffusion is driven by constituent gas ($CO_2$ and $H_2O$) concentration gradients between the system and ambient environment. Any time constituent gas concentrations inside the system are significantly different than ambient conditions, the diffusion potential increases. Metals, in nearly any practical working thickness, generally provide an outstanding diffusion barrier to gases. Practically, however, non-metallic materials are usually required. For example, to provide a seal between metallic materials, gaskets and O-rings are used. Flexible tubing which connects the sensor head to other system components is an example of functional capabilities which cannot be reasonably achieved with metals.

Figure 1A:
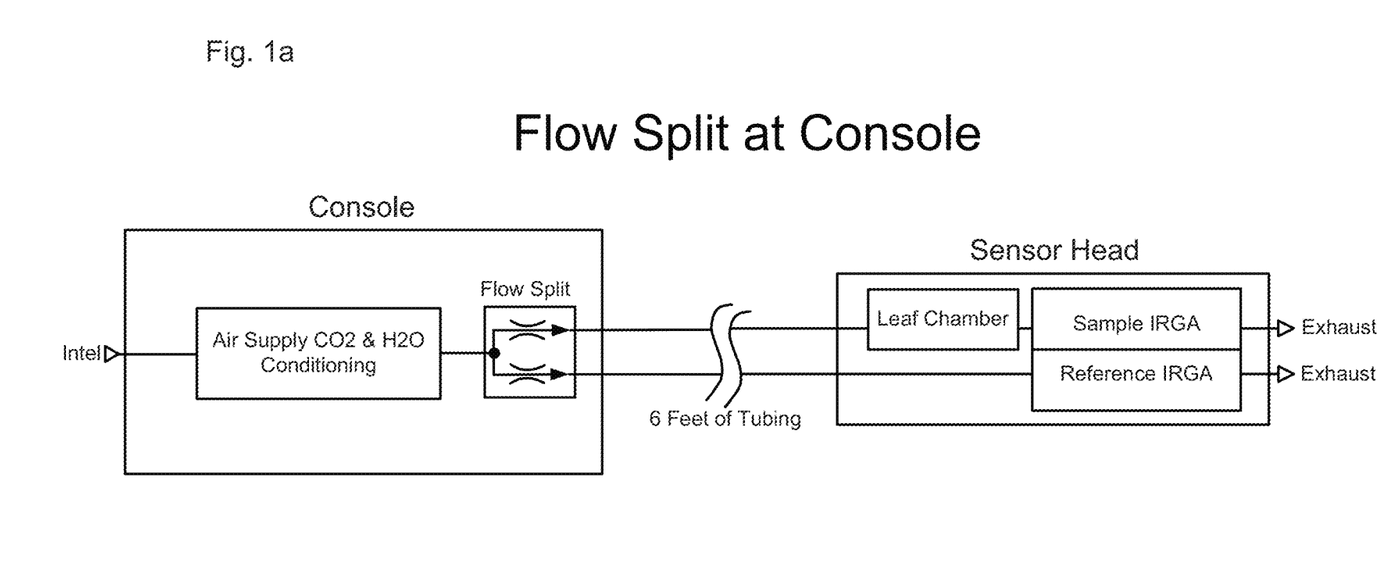
FIG. 1*a* illustrates the flow path in a prior photosynthesis measurement system where the flow is split at the console, remote from the sensor head.

In open photosynthesis systems, a conditioned air stream is typically split into two streams. FIG. 1a illustrates the flow path in such an open system where the flow is split at the console, remote from the sensor head, and flows to the sensor head via two separate paths. The first flow path (known as reference) passes through a gas analyzer (e.g., Infra-Red Gas Analyzer or IRGA) which measures constituent gas concentrations ($CO_2$ and $H_2O$). The second flow path (known as sample) passes through a sample chamber (leaf chamber) in which gas exchange occurs. This second sample flow path exits the chamber and enters a second gas analyzer (e.g., IRGA). The difference between the sample and reference gas concentrations is used to calculate photosynthesis ($CO_2$) and transpiration ($H_2O$). As photosynthesis and transpiration measurements are based on concentration differences in these two gas streams, the accuracy in measuring the difference is more critical than measuring the absolute concentration of either. Diffusive parasitic sources and/or sinks present in the tubing, connectors, and fittings that supply the head with the sample and reference gas streams can compromise measurement accuracy.

In practice, it is nearly impossible to fully eliminate parasitic sources and sinks due to diffusion. Therefore it is desirable to provide systems and methods that minimize the impact of diffusion and/or sorption and that help overcome the above and other problems.

Additionally, chambers used in photosynthesis and transpiration measurements typically incorporate mechanisms for regulating sample temperature. Heat transfer to and from the sample is accomplished either through radiative heat transfer between the sample and chamber walls, convective heat transfer between the chamber air and the sample, or both. Inevitably, parasitic heat transfer occurs between the chamber and the surrounding environment, thereby compromising the efficiency of sample temperature control. It is also therefore desirable to provide solutions that allow for more energy efficient temperature control.

Moreover, in many photosynthesis measurement systems, such as portable photosynthesis measurement systems, the size and weight of the chamber are primary ergonomic considerations. For portable systems, the chamber is manually transported, placed, and sometimes held in place for the duration of the photosynthesis measurement. It is therefore also desirable to provide light-weight and cost-effective photosynthesis measurement systems.

BRIEF SUMMARY

The present invention provides systems and methods for measuring photosynthesis and transpiration rates.

Embodiments of the invention provide system flow path designs that help minimize the impact of diffusion. By reducing the magnitude of parasitic source and sinks, lower rates of photosynthesis and transpiration can be more accurately measured, e.g., without the need for extensive empirical compensation. Embodiments also provide solutions to thermally insulate the chamber from the surrounding environment to advantageously enable more energy efficient temperature control, or alternatively, a wider range of temperature control using the same power as an un-insulated chamber and concomitantly provide an enhanced gas diffusion/sorption barrier.

Embodiments herein provide chamber systems and methods of constructing chambers which provide advantages over traditional chamber systems, such as, for example, reducing the power required for temperature control by using materials with significantly reduced (e.g., 1,000 times lower) thermal conductivity than traditional chamber materials, utilizing manufacturing methods which allow the creation of intricate, internal, leak-free paths for gas flow without introducing any significant additional manufacturing expense, and/or reducing the weight of the chamber by using materials which are significantly lighter (e.g., about 50% less dense) than traditional chamber materials.

According to one aspect of the present invention, a sensor head for use in a gas exchange measurement system is provided. The sensor head typically includes a sample chamber defining a measurement volume for analysis of a sample, the sample chamber having an inlet and an outlet, and a flow splitting mechanism located proximal to the sample chamber, the mechanism configured to split a gas flow received at an input port from a remote source to a first output port and to a second output port, wherein the first output port is coupled with the inlet of the sample chamber. The sensor head also typically includes a first gas analyzer coupled with the outlet of the sample chamber and configured to measure a concentration of one or more gases, and a second gas analyzer coupled with the second output port of the flow splitting mechanism and configured to measure a concentration of the one or more gases. Advantageously, gas diffusion sources and sinks, which differentially affect gas concentrations, are reduced due to the proximity of the flow splitting mechanism with the sample chamber and gas analyzers. This advantageously reduces measurement error associated with or attributable to gas diffusion sources and sinks. The proximity advantage derives from minimizing the joints, gaskets, fittings, tubing lengths, and materials all prone or susceptible to gas diffusion. In certain aspects, the one or more gases measured by the first and second gas analyzers includes $CO_2$ or $H_2O$.

According to another aspect of the present invention, a method is provided for measuring a gas concentration differential in a gas exchange analysis system having a sensor head having a sample chamber defining a measurement volume for sample analysis, the sample chamber having an inlet and an outlet, and a flow splitting mechanism located proximal to the sample chamber. The method includes splitting a gas flow received from a remote source at an input port of the flow splitting mechanism to a first output port and to a second output port, wherein the first output port is coupled with the inlet of the sample chamber, measuring a concentration of one or more gases exiting the sample chamber using a first gas analyzer, and measuring a concentration of the one or more gases exiting the second output port of the flow splitting mechanism using a second gas analyzer. The method also includes determining a concentration differential of the one or more gases based on the first concentration and the second concentration, whereby measurement error associated with diffusion sources and sinks of said gas are reduced due to the proximity of the flow splitting mechanism to the sample chamber and gas analyzers. In certain aspects, the measured gases include $CO_2$ or $H_2O$.

According to yet another aspect of the present invention, a device is provided for variably splitting the flow of gas in a sensor head of a gas exchange analysis system. The device typically includes an input port, a first output port, a second output port and a flow splitting mechanism, the device being located proximal to a sample analysis chamber having a measurement volume, and gas analyzers. The flow splitting mechanism is typically configured to variably split a gas flow received at the input port from a remote source to the first output port and to the second output port, wherein the first output port is coupled via a flow path to an inlet of the sample analysis chamber. The flow volume created by the measurement volume and the flow path is sufficiently small such as to reduce the time required to reach a steady state of gas concentrations in the flow volume when a flow ratio to the flow path is adjusted in the flow splitting mechanism. In certain aspects, the flow splitting mechanism is configured to adjust the flow ratio such that the gas flow is about 0% to 100% to the first output port and the remaining 100% to 0% to the second output port.

According to yet a further aspect, a gas exchange analysis system is provided that typically includes a sample chamber defining a measurement volume for analysis of a sample, the sample chamber having an inlet and an outlet, wherein the internal surface(s) of the chamber defining the measurement volume are metal plated. The system also typically includes a source of gas coupled with the inlet of the sample chamber, and a gas analyzer coupled with the outlet of the sample chamber and configured to measure a concentration of one or more gases exiting the chamber, whereby the metal plated internal surface(s) of the chamber reduces sorption of the one or more gases within the chamber. In certain aspects, the metal includes nickel. In certain aspects, the metal plated internal surface(s) are formed using electroless nickel plating on the internal surface(s). In certain aspects, the internal surface(s) of the chamber comprises a plastic material and/or aluminum and/or a fiberglass reinforced laminated composite. In certain aspects, the metal includes tin. In certain aspects, an internal surface includes an epoxy/glass composite.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

The present invention provides systems and methods for measuring photosynthesis and transpiration rates with the ability to efficiently control sample temperature.

Figure 1B:
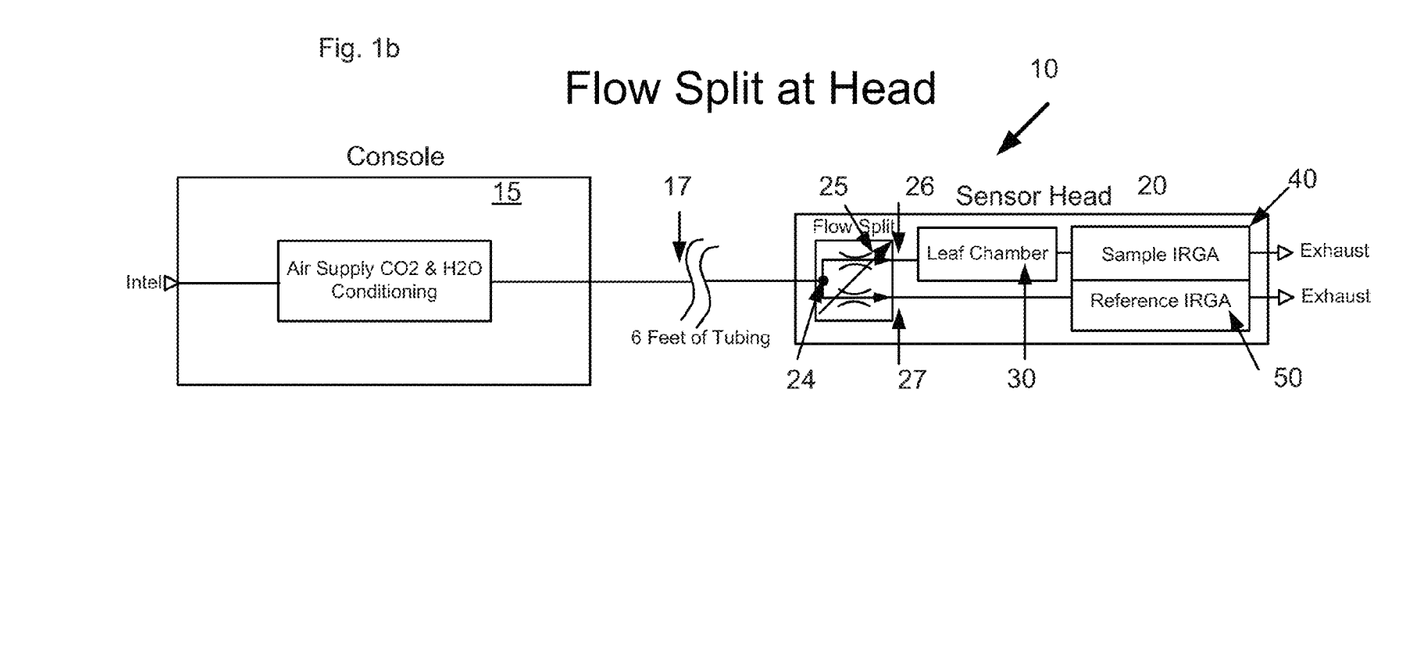
FIG. 1*b* illustrates a flow path in a photosynthesis measurement system according to one embodiment.

FIG. 1b illustrates a flow path in a gas exchange measurement system 10 according to one embodiment. Gas exchange measurement system 10 in one embodiment includes a console 15 and a sensor head 20 remote from console 15. Console 15 typically includes, or is connected with, one or more gas sources and gas conditioning equipment. For example, in the context of photosynthesis and transpiration measurements, gas sources would include reservoirs of $CO_2$ and $H_2O$, and conditioning equipment for conditioning each gas concentration. A flow path 17 connecting console 15 with sensor head 20 typically includes flexible tubing and connectors. Flow path 17 provides a single stream or gas flow path to flow splitting mechanism 25 in sensor head 20. Flow splitting mechanism 25 receives a stream of gas from console 15 and splits the flow into two separate flow paths as will be described in more detail below. One stream is provided to the sample chamber 30 (e.g., sample stream) and the other stream (e.g., reference stream) is provided to a reference gas analyzer 50. A second gas analyzer 40 receives and analyzes gas from chamber 30. Reference gas analyzer 50 and second gas analyzer 40 might each include an Infra-Red Gas Analyzer (IRGA), as is known in the art, or other gas analyzer. In general, the sample chamber can be used to house or hold a sample under investigation, such as a leaf, whole plant, conifer, soil, etc., and hence where "chamber", "sample chamber" or "leaf chamber" is used herein, such chamber is also intended to refer to a whole plant chamber, conifer chamber, soil chamber, etc. depending on the type of sample to be investigated.

It is desirable that flow path lengths and the number of connections downstream of the flow split device 25 be minimized to reduce parasitic sources and sinks which differentially affect concentrations in the two flow paths. Hence, according to one embodiment, the flow path is split in the sensor head proximal to the sample chamber. The majority of parasitic sources and sinks, which are located upstream of the sensor head in FIG. 1b, affect only a single air stream (flow path 17) when the flow is split at the sensor head 20. Parasitic sources and sinks which impact the sample and reference streams independently are advantageously minimized.

It is desirable that for a certain flow rate, through either the reference or sample path, less than a certain amount of diffusion occurs. As one example, for embodiments of the present invention, it is desirable that 0.1 μmole/mole (PPM) or less of $CO_2$ concentration change occur at a flow rate of about 50 μmol/sec in the sample leg. This corresponds to an effective diffusion rate of $CO_2$ of 5 pmoles/sec. For a given diffusion source/sink rate, as the flow rate increases, the concentration change due to the diffusion source/sink has a smaller concentration effect; concomitantly, a given diffusion source/sink has a greater effect on concentration at a smaller flow rate. Hence, as above, it is desirable to minimize the flow path lengths having diffusion-susceptible material and components to reduce or minimize parasitic sources and sinks of gases. One way to do this is to minimize the flow path length itself. An additional, or alternate, way is to reduce or minimize components of the flow path that are diffusion-susceptible. In practice, however, certain diffusion-susceptible materials and components are used for cost and efficiency reasons. Therefore, according to one embodiment, the flow is split as close to the sample chamber and gas analyzers as possible. In certain aspects, the flow splitting mechanism 25 is located such that a minimal amount of flow path having components or surface areas exposed or susceptible to diffusion exists between the flow splitting device 25 and the sample chamber 30. The desired length of the flow path is generally a function of the flow rate and the diffusion susceptible material or components making up the flow path; for example, for metal tubing, the flow path can be significantly longer than for plastic or other diffusion-susceptible components. For example, in certain aspects, a flow path having 12" or less of diffusion-susceptible tubing and/or other components is desirable to couple the flow splitting mechanism 25 with the sample chamber 30 to provide a gas stream flow path from the splitting mechanism. In other aspects, less than about 6", or 4" or 2" or even 1" or less of such diffusion-susceptible flow path exists between the flow splitting device 25 and the sample chamber 30.

Similarly, in certain aspects, the flow splitting mechanism is located in the sensor head such that less than about 12" of such diffusion-susceptible flow path exists between the flow splitting device 25 and the reference gas analyzer 50. In other aspects, the flow splitting mechanism is located such that less than about 6", or 4" or 2" or even 1" or less of such flow path exists between the flow splitting device 25 and the reference gas analyzer 50. It is also desirable that that flow path length between the sample chamber 30 and sample gas analyzer 40 be minimized. One skilled in the art will appreciate that the diffusion-susceptible flow path from the flow splitting mechanism 25 to the reference gas analyzer 50 can be roughly the same length as the diffusion-susceptible flow path from the splitting mechanism 25 through the sample chamber 30 to the sample gas analyzer 40. Alternately, the two diffusion-susceptible flow paths can be different lengths as desired.

Figure 2:
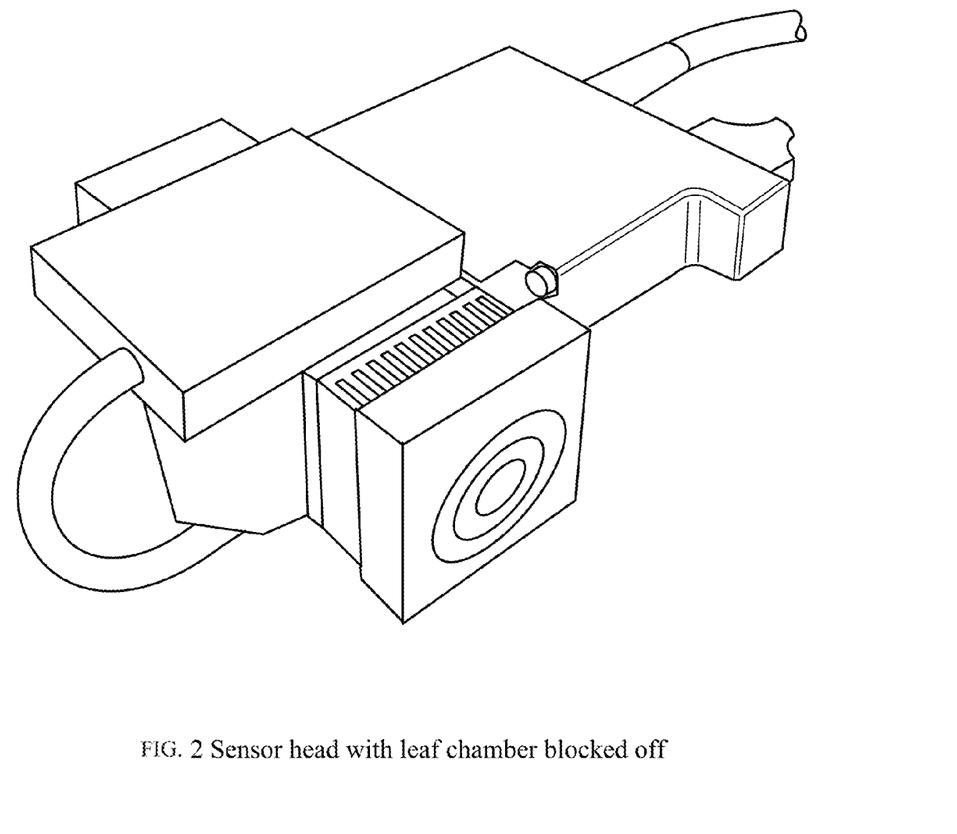
FIG. 2 illustrates a chamber removed from the LI-COR Biosciences LI-6400 instrument head (see, e.g., FIG. 1*a*) and replaced with an aluminum block and a vinyl gasket.
Figure 3:
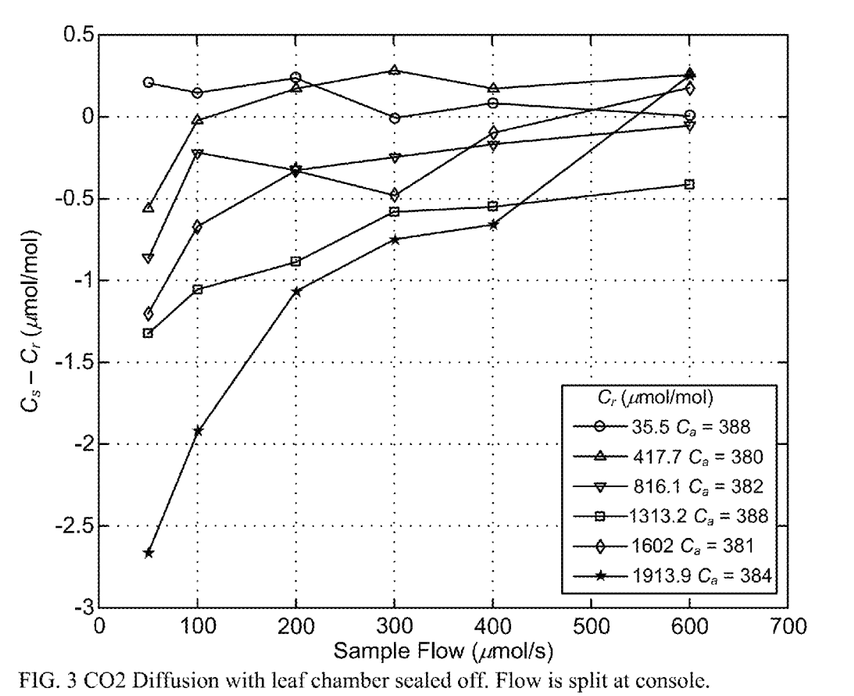
FIG. 3 shows the results of the experiment with the configuration in FIG. 2, using the experimental protocol outlined in the LI-COR Biosciences LI-6400 User Manual (pp 4-43 through 4-48; included herein as Appendix A).
Figure 4:
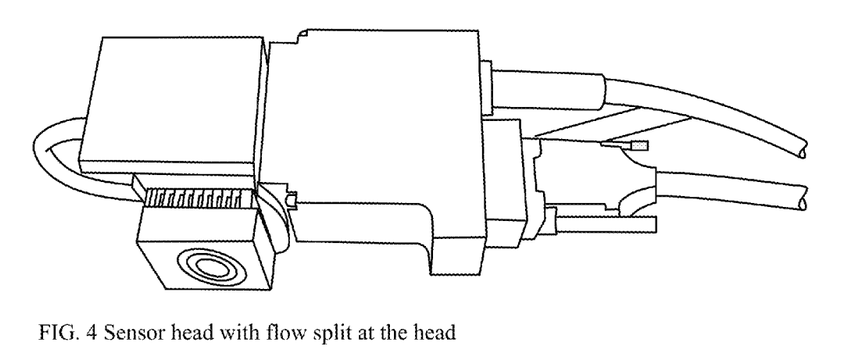
FIG. 4 illustrates a different perspective view of the sensor head of FIG. 2

Experiments using the LI-COR Biosciences LI-6400 have verified that diffusion through flexible tubing, gaskets, and pneumatic connectors is a significant and quantifiable issue. In one experiment, to eliminate diffusion sources/sinks from the leaf chamber, the chamber was removed from the LI-6400 head (see, e.g., FIG. 1a) and was replaced with an aluminum block and a vinyl gasket as shown in FIG. 2. FIG. 4 illustrates a different perspective view of the sensor head of FIG. 2. FIG. 3 shows the results of the experiment with the configuration in FIG. 2, using the experimental protocol outlined in the LI-6400 User Manual (pp 4-43 through 4-48; included herein as Appendix A). FIG. 3 shows there are significant differences between the sample (Cs) and reference (Cr) concentrations of $CO_2$ in the absence of a leaf. The differences shown in FIG. 3 are due exclusively to parasitic sources and sinks of $CO_2$. As there were no known bulk leaks during the experiment, the differences shown in FIG. 3 are dominated by diffusion. The magnitude of the concentration difference is largest at low flow rates and at large $CO_2$ concentrations (relative to ambient Ca).

FIG. 3 demonstrates that the diffusive parasitic sources and/or sinks can be attributed to system components other than the sample chamber and gaskets. The diffusion source and/or sink must be present in the tubing, pneumatic connectors and fittings that supply the head with the sample and reference gas streams.

A difference in sample and reference flow rates causes a difference in concentrations even if the diffusive rates are approximately equal. FIG. 3 shows that at low sample flow rates, and a given stream concentration, the concentration difference (Cs–Cr) is more pronounced than at higher sample flow rates. For example, at a nominal concentration of 1913.9 PPM of $CO_2$, (Cs–Cr) is approximately −2.6 PPM at the lowest flow rate. Ambient $CO_2$ concentration is approximately 384 PPM. Under these flow conditions, the sample flow rate is much lower than the reference flow rate, and diffusion reduces the concentration of the sample much more than the reference, resulting in the negative value of (Cs–Cr). The reduction occurs because of diffusive parasitic sinks, whereas at a nominal concentration of 35.5 PPM (below ambient Ca of 388 PPM), the values of (Cs–Cr) are positive, and parasitic diffusion acts as a source.

Splitting the flow at the sensor head, according to one embodiment, reduces the number of components (e.g., tubing, connectors and fittings), and the pneumatic path length, subjected to parasitic $CO_2$ sources and/or sinks, thereby reducing the magnitude of the difference in (Cs–Cr) due to systematic issues. The advent of smaller pneumatic components, including MEMS-based mass flow meters, has enabled a practical implementation of splitting the flow path in the sensor head. One useful flow meter is produced by Omron, e.g., part number D6F-02A3.

In one embodiment, the flow splitting mechanism 25 is configured to variably split the flow of gas in the sensor head. In particular, the flow splitting mechanism is configured to variably split a gas flow received at the input port 24 from a remote source (console 15) to a first output port and to the second output port as shown in FIG. 1b. The second output port is coupled via a flow path 27 with an inlet of the second IRGA 50. The first output port is coupled via a flow path 26 with an inlet of the sample analysis chamber 30. A flow volume, including the measurement volume in the sample chamber 30 and the flow path, is sufficiently small such as to reduce the time required to reach a steady state of gas concentrations in the flow volume when a flow ratio to the flow path is adjusted in the flow splitting mechanism. For example, the measurement volume might be on the order of 1 mL to 10 mL to about 1000 mL, such that the flow path including the flow volume between the flow splitting device and the sample IRGA 40 might be smaller than, or on the order of, about 20 mL to about 1000 mL. In certain aspects, the flow splitting mechanism is configured to adjust the flow ratio such that the gas flow can be controllably, and continuously, varied to provide a flow range of between about 0% to 100% to the first output port and the remaining 100% to 0% to the second output port. For example, the flow splitting mechanism can be controlled via a control signal to split the flow 25% to one of the first port or second output port and 75% to the other output port, or 50% to one output port and 50% to the other output port.

Figure 5:
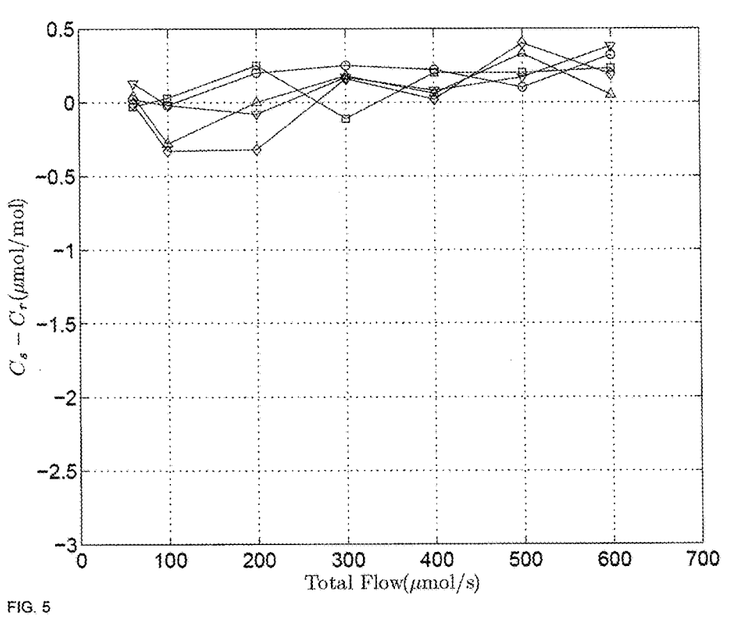
FIGS. 5 and 6 illustrate results of an experiment that shows a significant reduction in the CO2 concentration difference (Cs–Cr) between the sample and reference.
Figure 6:
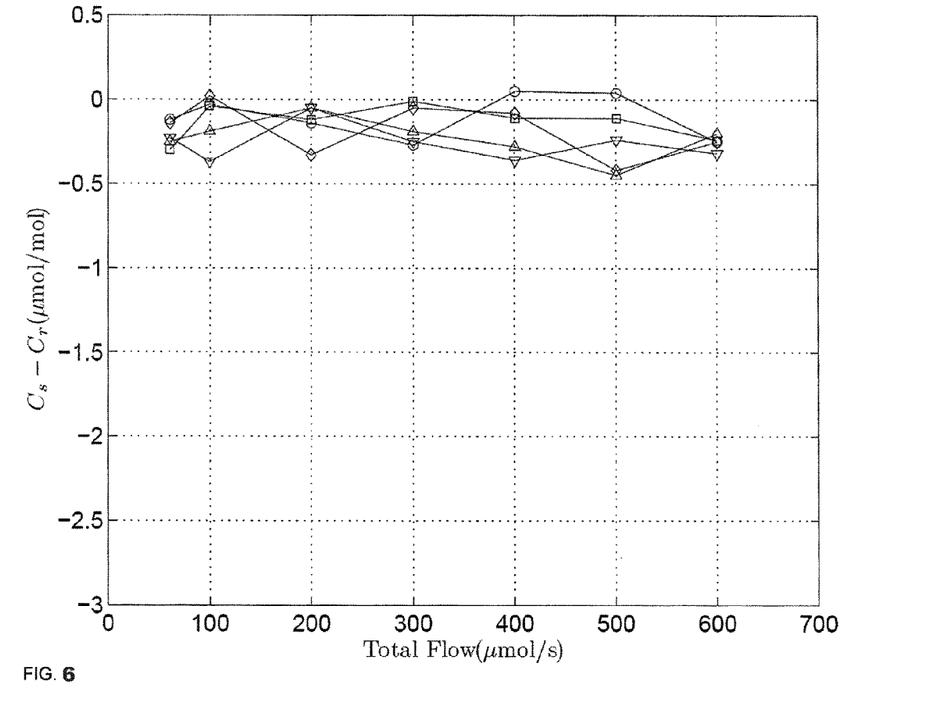

Experiments were conducted with an approximate 50%-50% flow split (50% of flow to reference, 50% to sample) and a 75%-25% flow split (75% to reference, 25% to sample) at the head of a LI-6400 instrument. The results (FIG. 5 and FIG. 6) show a significant reduction in the $CO_2$ concentration difference (Cs–Cr) between the sample and reference. The $CO_2$ concentration inside the IRGA was roughly 1940 μmol/mol for the experiments of FIG. 5 and FIG. 6. Comparing FIG. 3 (Cr=1913.9 μmol/mol) with FIG. 6 demonstrates that splitting the flow at the head can reduce diffusion effects by nearly an order-of-magnitude.

Figure 7:
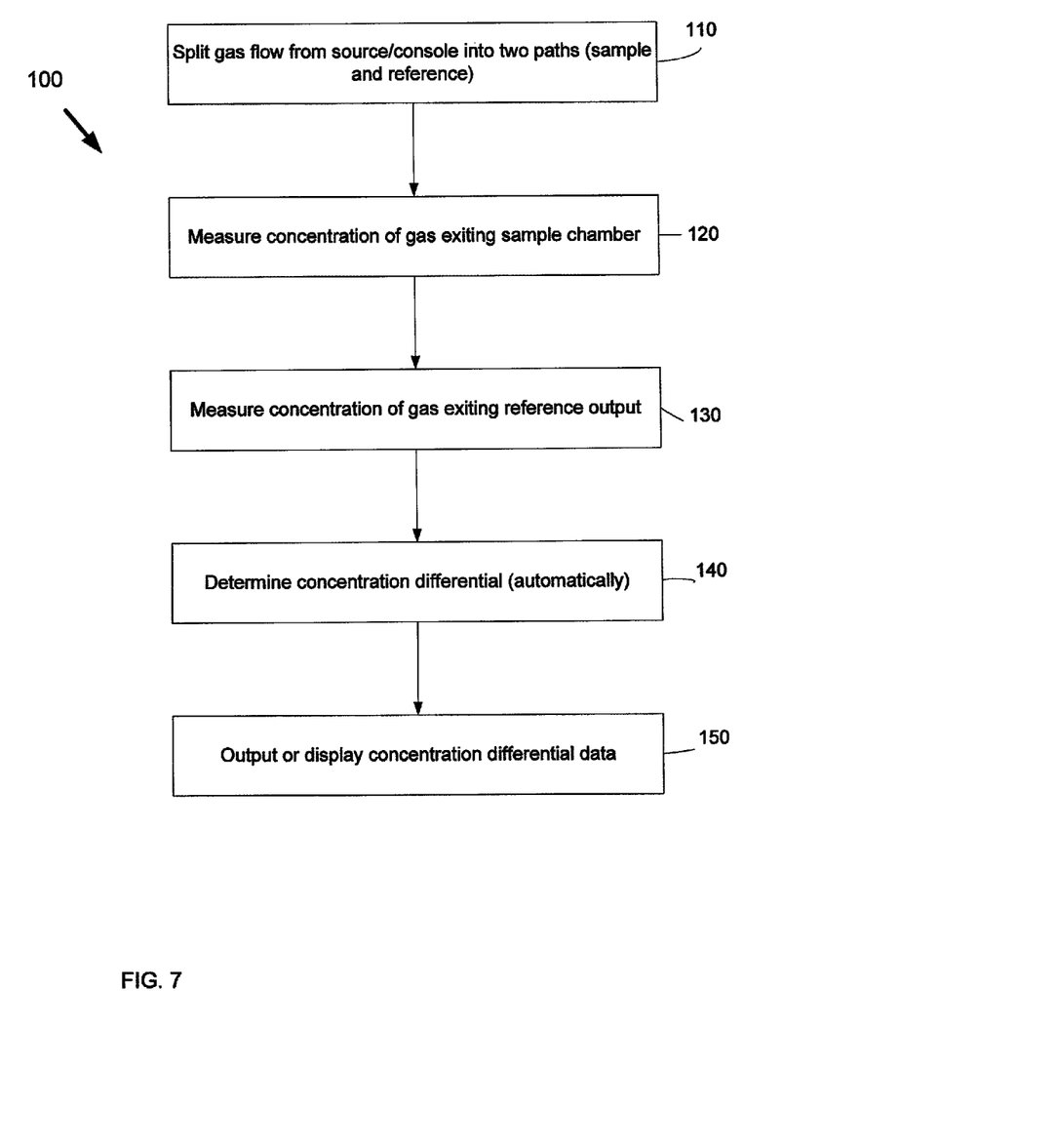
FIG. 7 illustrates a method of measuring a concentration differential of a gas in a gas exchange analysis system according to one embodiment.

FIG. 7 illustrates a method 100 of measuring a concentration differential of a gas in a gas exchange analysis system according to one embodiment. The gas exchange analysis system includes a sensor head having a flow splitting mechanism located proximal to a sample chamber that defines a measurement volume for analysis of a sample. The sample chamber includes an inlet and an outlet, with the inlet being connected, in close proximity, with an output port of the flow splitting device. The outlet is connected, also preferably in close proximity, with a gas analyzer such as an IRGA. In step 110, a gas flow received from a remote source at an input port of the flow splitting mechanism is controllably split to a first output port and to a second output port, with the first output port being coupled with the inlet of the sample chamber. In step 120, a first concentration of one or more gases exiting the sample chamber is measured using a first gas analyzer (e.g., gas analyzer 40) fluidly coupled with an output of the sample chamber. In step 130, a second concentration of the one or more gases exiting the second output port is measured using a second gas analyzer (e.g., gas analyzer 50) fluidly coupled with the second output port of the flow splitting device. In step 140, a concentration differential of the one or more gases is determined based on the first measured concentration and the second measured concentration. Step 140 can be performed using a processor or computer system that is integrated in the sensor head and/or in the console of the gas analysis system and/or in a remote computer system that is communicably coupled with the gas analysis system. In step 150, the concentration differential is output, e.g., displayed on a monitor or other output device, printed, stored, or otherwise provided to another computer system or device. Advantageously, measurement error associated with diffusion sources and sinks of the gas are reduced due to the proximity of the flow splitting mechanism with the sample chamber.

Insulated Sample Chamber

According to one embodiment, Selective Laser Sintering (SLS) or Fused Deposition Modeling (FDM) of plastic materials, such as nylon (SLS), glass-filled nylon (SLS) and Acrylonitrile Butadiene Styrene (or ABS) (FDM), is used to produce sample chambers and other system components. Alternative Direct Digital Manufacturing (DDM) techniques and materials may be used as they become available. In one embodiment, electro-less nickel plating of plastic materials is used, e.g., to avoid the sorption problems which might occur with raw SLS, FDM or epoxy-glass composite chambers.

Both Selective Laser Sintering (SLS) and Fused Deposition Modeling (FDM) are technologies developed in the field of rapid-prototyping. These technologies are being expanded beyond prototypes to functional product components. When these technologies are employed in the manufacture of a product, they are classified as Direct Digital Manufacturing (DDM). Key advantages of DDM methods include:
1. nearly arbitrary geometry can be created without the limitations of traditional material removal machining processes (milling, turning, drilling, etc.),
2. complex geometry can be created directly from a CAD model without the time and tooling costs associated with molded parts, and
3. complex internal geometry can be created that is not possible with any other conventional manufacturing process (machining or molding).

Also, the flexibility of these DDM processes allows single parts with intricate internal passageways to be created. These internal passageways can be optimized, for example, so that the flow around the sample is optimized for both gas and heat exchange with the sample.

As the field of DDM evolves, there is a steady introduction of new materials and improved processes. According to one embodiment, one useful, currently available material is a glass-filled nylon. The glass fill provides an increase in part strength, as well as a modest decrease in the linear thermal expansion coefficient. A few significant material properties are shown in Table 1 below. Although there are no currently published material properties for the glass-filled nylon composite used for testing, it is reasonable to expect that the material properties of the composite material will lie between those individual materials properties for glass and nylon. The following material property comparisons are significant.

1. The glass-filled nylon will have a density ranging from 7% (pure glass) to 57% (pure nylon) less than aluminum, making a composite chamber lighter weight than a comparable aluminum chamber. The final value depends on the glass-fill ratio, but typical density values of glass-filled nylon composites are 1.4 g/cm^3 (e.g., about 48% less dense than aluminum).
2. The glass-filled nylon will have a thermal conductivity between about 240 and 1,000 times less than aluminum. The exact number again depends on the glass-fill ratio, but it is anticipated the end value will be close to about 1,000 times less.
3. The glass-filled nylon is expected to have a linear thermal expansion coefficient somewhere between that of pure glass (8.5e-6/C) and pure nylon (23e-6/C). Exact values for particular composites have not yet been identified. Because electroless nickel plating occurs at elevated temperatures, it is advantageous if the material being plated has a thermal expansion coefficient close to that of nickel (13e-6/C). Conversely, electroless nickel plating of pure ABS (90e-6/C) may be more challenging because of the mismatched coefficients of thermal expansion. In one embodiment, a deposit of electro-less copper can be plated first to the glass-filled nylon, which serves as a bonding layer for the nickel. Once the copper layer is plated, nickel is plated to the copper.

TABLE 1

| Material | Density (g/cm^3) | Thermal Conductivity (W/(m * K)) @ 25 C. | Linear Thermal Expansion Coefficient (10^-6 in/in/C) |
|---|---|---|---|
| Aluminum | 2.7 | 250 | 23 |
| Nylon 6 | 1.15 | 0.25 | 23 |
| Glass | 2.5 | 1.05 | 8.5 |
| Nickel | 8.91 | 91 | 13.0 |
| ABS | 1.0 | 0.2 | 90 |

Alternative methods for depositing metal films upon non-metallic (e.g., plastic) substrates include vacuum deposition. Vacuum deposition requires a line-of-sight between the source of metal atoms and the target. Thus, coating internal passageways with vacuum deposition would be difficult at best. Vacuum deposition processes are also more expensive than conventional plating processes, as they require a vacuum chamber.

Figure 8:
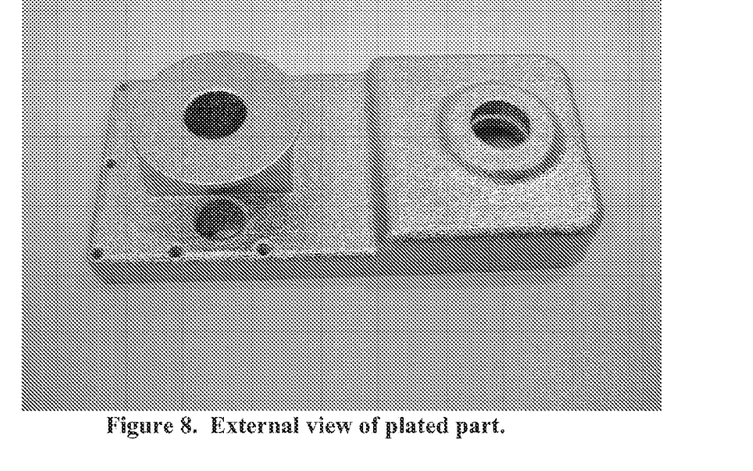
FIG. 8 shows an external view of a single nickel plated glass-filled nylon SLS part.
Figure 9:
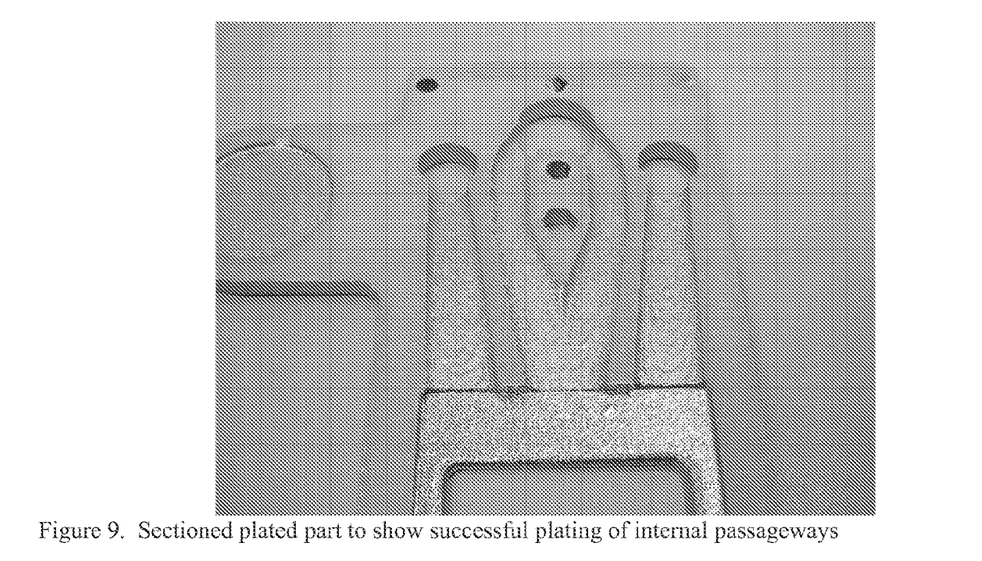
FIG. 9 shows a single part, different from that shown in FIG. 8, fabricated via SLS, and then electro-less nickel plated.

FIG. 8 and FIG. 9 illustrate the successful demonstration of various embodiments. FIG. 8 shows the external view of a single nickel plated glass-filled nylon SLS part. It is apparent in FIG. 8 that relatively complex geometry can be incorporated into a single SLS part. What may not be apparent in FIG. 8 is that the part contains internal passages which communicate flow from the left-hand side of the part to the right.

FIG. 9 illustrates how complex internal features can be created with the SLS process, and subsequently electro-less nickel plated. FIG. 9 shows a single part, different from that shown in FIG. 8, fabricated via SLS, and then electro-less nickel plated. The part contains three ports near the top of FIG. 9 which communicate with the sample chamber (rectangular area near the bottom of FIG. 9). Once the part was created and plated, the part was cut in half, approximately along the centerline of the channels which communicate gas between the three ports and the sample chamber. FIG. 9 clearly shows that these internal passages were completely plated by the electro-less nickel process.

As described above, certain of the advantages provided by the various embodiments include the ability to create complex and intricate flow passageways using SLS/FDM and other direct digital manufacturing technologies or laminated fiberglass reinforced epoxy composites; leveraging the extremely low thermal conductivity of nylon, ABS, other plastic and composite materials (e.g. FR4) to produce chambers that are lighter and that have more energy efficient sample temperature control; the direct use of nickel plated plastics or composites in the production of sample chambers; and a reduction in diffusion and sorption of gases due to the nickel plating.

In other embodiments, electroless nickel plating is used to coat metal parts, for example, traditionally, leaf chambers are constructed of light-weight aluminum. Bare aluminum naturally forms an oxide layer. This oxide layer is quite porous, and will retain and release water molecules through sorption. To combat water sorption in such aluminum chambers, the aluminum components are plated with nickel via Electroless Nickel Plating in certain embodiments. The thin layer of nickel deposited on the surface of the aluminum substrate greatly reduces water sorption. Also, electroless plating provides nearly uniform thickness on complex parts, unlike electroplating, in which plating thickness can change depending on exposure to electrical fields during plating. Other plating options (e.g. tin) may be more cost-effective on the epoxy/glass composites.

According to another embodiment, techniques used in the art to construct multi-layer fiberglass reinforced epoxy composite circuit boards can be used to create chambers and manifolds. Layering acrylic sheets with machined manifold pathways is well known in the art for creating complex pneumatic circuits. Acrylic sheets are selectively machined and subsequently bonded by either solvent or diffusion bonding. Traditional multi-layer fiberglass reinforced epoxy circuit boards are made in much the same way, using layers of fiberglass reinforced epoxy sheets (e.g. FR4), machined, selectively plated, and then laminated together with epoxy. Although traditional laminated printed circuit board (PCB) manufacturing technology does not offer the same geometric flexibility as other Direct Digital Manufacturing (DDM) processes, it is highly automated, flexible, and therefore cost effective. Moreover, plating of copper, nickel, and tin onto the substrates used in PCB manufacture are well understood in the art, and well demonstrated in practice.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas exchange analysis system, comprising:
  a sample chamber defining a measurement volume for analysis of a sample, the sample chamber having an inlet and an outlet, wherein the internal surface(s) of the chamber defining the measurement volume comprises a nickel plated plastic material;
  a source of gas coupled with the inlet of the sample chamber;

a gas analyzer coupled with the outlet of the sample chamber and configured to measure a concentration of one or more gases exiting the chamber;

whereby the nickel plated internal surface(s) of the chamber reduces sorption of the one or more gases within the chamber.

2. The system of claim 1, wherein the source of gas includes a gas conduit coupled with a gas reservoir.

3. The system of claim 2, wherein the reservoir is located remote from the sample chamber.

4. The system of claim 1, wherein the nickel plated internal surface(s) are formed using electroless nickel plating on the internal surface(s).

5. The system of claim 1, wherein the plastic material is selected from the group consisting of nylon, glass-filled nylon and Acrylonitrile Butadiene Styrene (ABS).

6. The system of claim 1, wherein said one or more gases measured by the gas analyzer includes $CO_2$ and $H_2O$.

7. The system of claim 1, wherein the gas analyzer includes an Infra-Red Gas Analyzer (IRGA).

8. The system of claim 1, wherein the internal surface(s) of the chamber comprises a fiberglass reinforced laminated composite.

9. The system of claim 1, wherein the sample includes one of a leaf, a whole plant, a conifer or soil.

10. A gas exchange analysis system, comprising:
a sample chamber defining a measurement volume for analysis of a sample, the sample chamber having an inlet and an outlet, wherein the internal surface(s) of the chamber defining the measurement volume comprises a nickel plated material selected from the group consisting of nylon and a glass-filled nylon;

a source of gas coupled with the inlet of the sample chamber;

a gas analyzer coupled with the outlet of the sample chamber and configured to measure a concentration of one or more gases exiting the chamber;

whereby the nickel plated internal surface(s) of the chamber reduces sorption of the one or more gases within the chamber.

11. A gas exchange analysis system, comprising:
a sample chamber defining a measurement volume for analysis of a sample, the sample chamber having an inlet and an outlet, wherein the internal surface(s) of the chamber defining the measurement volume comprises a nickel plated fiberglass reinforced laminated composite material;

a source of gas coupled with the inlet of the sample chamber;

a gas analyzer coupled with the outlet of the sample chamber and configured to measure a concentration of one or more gases exiting the chamber;

whereby the nickel plated internal surface(s) of the chamber reduces sorption of the one or more gases within the chamber.

* * * * *